United States Patent
Whitcher et al.

(10) Patent No.: US 8,468,839 B2
(45) Date of Patent: Jun. 25, 2013

(54) PORTABLE LIQUID OXYGEN STORAGE UNIT

(75) Inventors: Douglas Whitcher, Woodstock, GA (US); Robert J. Maddox, Jr., Catersville, GA (US); Joseph T. Dolensky, Kennesaw, GA (US)

(73) Assignee: RIC Investments, LLC, Wilmington, DE (US)

( * ) Notice: Subject to any disclaimer, the term of this patent is extended or adjusted under 35 U.S.C. 154(b) by 1062 days.

(21) Appl. No.: 12/018,503

(22) Filed: Jan. 23, 2008

(65) Prior Publication Data
US 2008/0178610 A1 Jul. 31, 2008

Related U.S. Application Data

(60) Provisional application No. 60/898,307, filed on Jan. 30, 2007.

(51) Int. Cl.
*F17C 7/04* (2006.01)
*F17C 9/02* (2006.01)

(52) U.S. Cl.
USPC .............................. 62/48.1; 62/49.1; 62/50.2

(58) Field of Classification Search
USPC .... 62/48.1, 49.1, 49.2, 50.1, 50.2; 137/15.18, 137/15.17, 15.22, 413, 588
See application file for complete search history.

(56) References Cited

U.S. PATENT DOCUMENTS

| | | | |
|---|---|---|---|
| 2,528,822 A * | 11/1950 | Dunn | 251/54 |
| 3,707,078 A | 12/1972 | Cramer | |
| 4,211,086 A * | 7/1980 | Leonard et al. | 62/48.1 |
| 4,423,750 A * | 1/1984 | Morizumi et al. | 137/413 |
| 4,625,753 A | 12/1986 | Gustafson | |
| 4,956,975 A | 9/1990 | Gustafson | |
| 5,228,585 A | 7/1993 | Lutgen et al. | |
| 5,373,702 A | 12/1994 | Kalet et al. | |
| 5,404,918 A | 4/1995 | Gustafson | |
| 5,421,161 A | 6/1995 | Gustafson | |
| 5,421,162 A | 6/1995 | Gustafson et al. | |
| 5,572,875 A | 11/1996 | Gustafson | |
| 5,893,275 A | 4/1999 | Henry | |
| 6,128,908 A | 10/2000 | Gustafson | |

(Continued)

OTHER PUBLICATIONS

Respironics, Inc., "Many Questions About Liquid Oxygen", brochure.

(Continued)

*Primary Examiner* — Frantz Jules
*Assistant Examiner* — Webeshet Mengesha
(74) *Attorney, Agent, or Firm* — Michael W. Haas

(57) ABSTRACT

A portable liquid oxygen (PLOX) unit and method of filling. The LOX unit includes a LOX container. An inlet line communicates LOX from a LOX supply to an the LOX container, and an outlet line communicates LOX from the LOX container ultimately for consumption by a user. A vent line communicate the interior of the LOX container to ambient atmosphere. A vent valve is coupled to the vent line to selectively communicate the LOX container to the ambient atmosphere. An auto shutoff assembly is associated with vent line to substantially block the vent line when the LOX in the LOX container reaches a predetermined level. A reset element associated with the auto shutoff assembly causes at least a portion of the auto shutoff assembly to unblock the vent line for subsequent filling.

27 Claims, 9 Drawing Sheets

U.S. PATENT DOCUMENTS

| | | | |
|---|---|---|---|
| 6,393,847 B1 | 5/2002 | Brooks et al. | |
| 6,651,659 B2 | 11/2003 | Izuchukwu | |
| 6,698,423 B1 | 3/2004 | Honkonen et al. | |
| 6,742,517 B1 | 6/2004 | Frye et al. | |
| D528,212 S * | 9/2006 | Conway et al. | D24/164 |
| 2006/0219245 A1 | 10/2006 | Holder | |
| 2007/0039616 A1 | 2/2007 | Hughes et al. | |

OTHER PUBLICATIONS

Healthdyne Technologies, "Service Manual for Protégé Stationary Portable liquid oxygen units".

Nellcor Puritan Bennett Inc., "HELiOS H300 Personal Oxygen System Filling Guide", 2003.

* cited by examiner

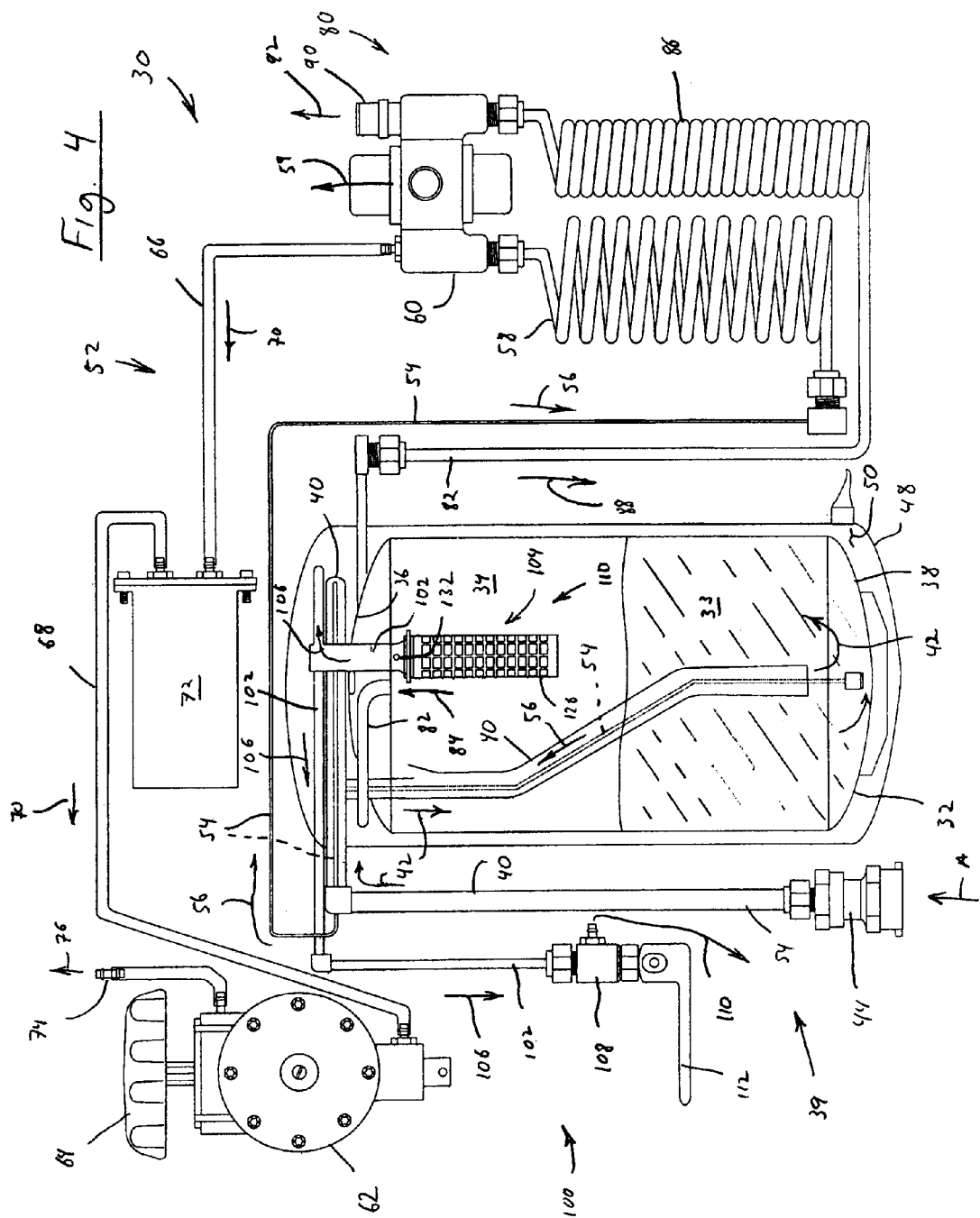

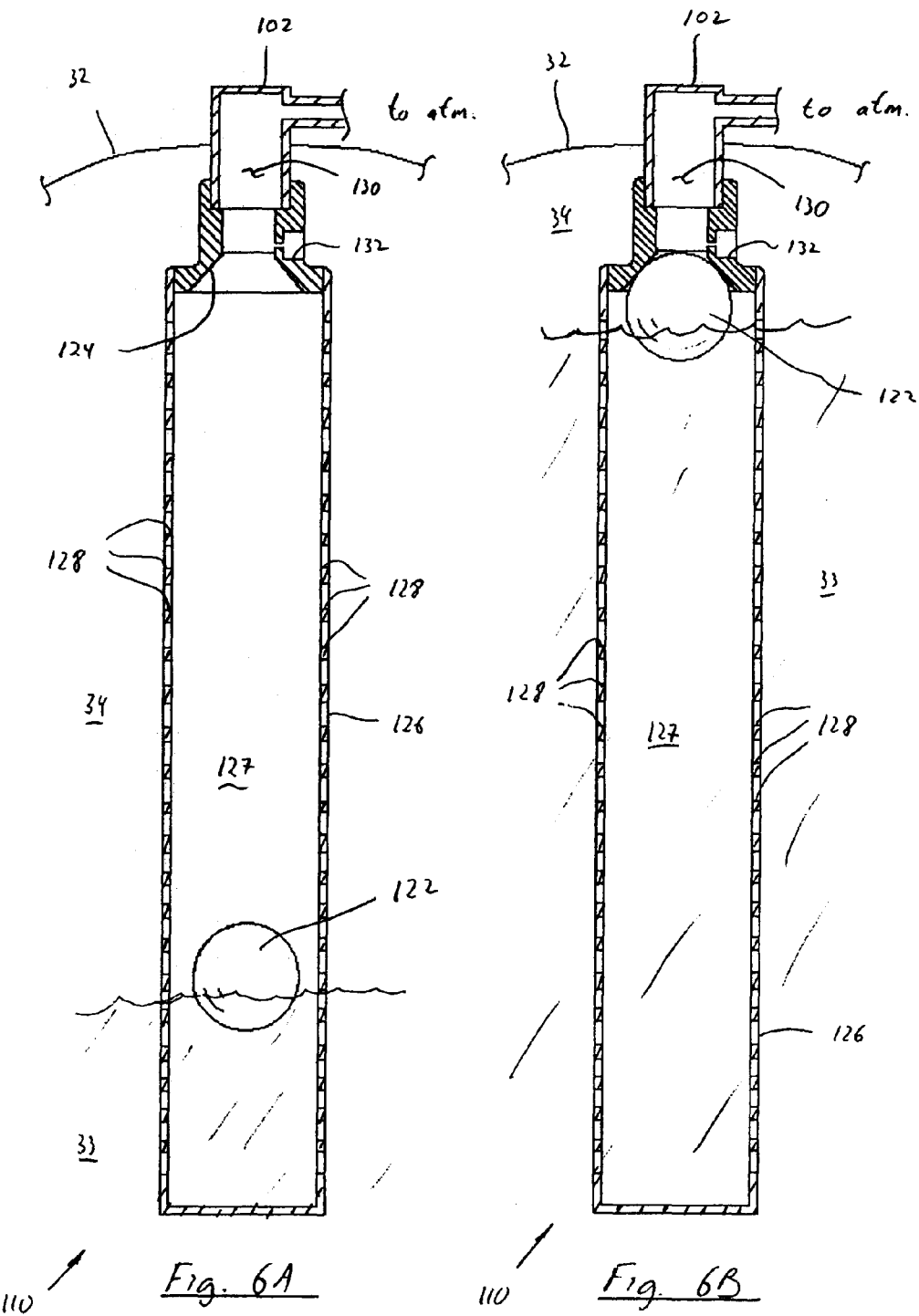

PORTABLE LIQUID OXYGEN STORAGE UNIT

CROSS-REFERENCE TO RELATED APPLICATIONS

This application claims priority under 35 U.S.C. §119(e) from provisional U.S. patent application No. 60/898,307 filed Jan. 30, 2007 the contents of which are incorporated herein by reference.

BACKGROUND OF THE INVENTION

1. Field of the Invention

The present invention pertains to a system and method for filling a portable liquid oxygen (PLOX) unit, and, in particular, to such a system and method that automatically shuts off the flow of LOX to the PLOX unit and allows for "hands free" filling.

2. Description of the Related Art

The delivery of supplemental oxygen to a patient is typically prescribed for individuals suffering from pulmonary/respiratory problems. The prescription and delivery of supplemental oxygen is undertaken to ensure that sufficient oxygen levels are received by the patient. Situations where supplemental oxygen may be prescribed include individuals afflicted with a chronic obstructive pulmonary disease, such as asthma, as well as individuals suffering from diseased or damaged lungs.

It is known to deliver supplemental oxygen using a liquid oxygen ("LOX") system. A conventional LOX system includes a large stationary LOX storage canister that is located at and remains at the user's home. The stationary LOX canister is replenished periodically from a mobile LOX storage vessel, which is typically a truck carrying a large quantity of LOX. A conventional LOX system also includes a small, portable delivery apparatus weighing from five to thirteen pounds that can be filled from the stationary unit for trips outside the home.

The portable delivery apparatus converts the liquid oxygen to a breathable gas for consumption by the user. These systems have limited utilization due to the low LOX capacity of the portable delivery apparatus and the administered LOX flow rate. Furthermore, even when not in use, the LOX within the portable delivery apparatus evaporates at a typical rate of one pound per day, empting the portable delivery apparatus LOX supply over time even if it is not used. Consequently, when using a portable LOX system, the user must return to the LOX supply to refill the portable delivery apparatus.

One such LOX system is disclosed in U.S. Pat. No. 6,742,517 ("the '517 patent") entitled, High Efficiency Liquid Oxygen Storage and Delivery System. As disclosed in this patent, a typical LOX system includes a stationary LOX storage canister located in an individual's home and a portable LOX delivery unit that the patient uses outside the home. The stationary LOX storage canister must be periodically refilled with LOX by a distributor via a truck, van, or other vehicle capable of carrying a large quantity of liquid oxygen. The name of the portable delivery unit in the commercial implementation of this LOX system and described in the '517 patent is the HELiOS300. As identified at the HELiOS website, www.heliosoxygen.com, the HELiOS H300 portable LOX delivery unit has a limited capacity for storing liquid oxygen. This capacity is limited to eight to ten hours of usage, after which the LOX is depleted.

The HELiOS system is refilled by firmly forcing the HELiOS H300 portable LOX delivery unit onto the LOX storage canister by pressing down on the HELiOS H300 portable LOX delivery unit to cause it to engage with the LOX storage canister. While forcing the HELiOS H300 portable LOX delivery unit onto the LOX storage canister the user must manually move a vent valve level on the exterior of the portable deliver unit to an open position. This requires simultaneously applying a downward force on the HELIOS H300 portable LOX delivery unit and moving the valve level. Naturally, this requires using both hands or using more than one person to fill the portable delivery unit.

During filling, the user must maintain a watch on the HELiOS H300 portable LOX delivery unit until sputtering in the filling noise associated with the filling of the unit. In addition, the user must watch for the release of white vapor from the HELiOS H300 portable LOX delivery unit in order to ensure that the unit has been completely filled. After which, the user is instructed to release the portable LOX delivery unit from the storage canister.

In another system, such as the Stroller/Spirit sold by Caire, Inc., the portable LOX delivery unit can be attached to the LOX storage canister. However, the user must still maintain a vigil over the portable LOX delivery unit to determine when the unit has been filled. Again, this requires that the user discern a change in the sound associated with the filling of the unit and visually notice a white cloud being released by the unit.

It can be appreciated that conventional processes for filling a portable liquid oxygen system have two main problems. Firstly, they are quite cumbersome and difficult for most users. Many systems, such as process for filling the HELiOS H300 portable LOX delivery unit, require the users to use one or both hands to fill the system, which can be quite difficult for them to accomplish. This is especially true for users with limited strength or dexterity. Secondly, they require the user to determine when the system is full based on sound changes and/or white clouds of oxygen gas and small amounts of liquid venting from the system. This type of filling process is ambiguous at best for the user to know whether the system has actually been filled to the appropriate liquid level. If the user is audibly and/or visually impaired, the process can be quite problematic for the user.

SUMMARY OF THE INVENTION

Accordingly, it is an object of the present invention to provide a portable liquid oxygen (PLOX) unit that overcomes the shortcomings of conventional portable liquid oxygen delivery units. This object is achieved according to one embodiment of the present invention by providing a PLOX unit that includes a LOX container having an interior, and inlet line, an outlet line, and a vent line. The inlet line is adapted to communicate LOX from a LOX supply to the interior of the LOX container. The outlet line is adapted to communicate LOX from the interior of the LOX container. The vent line is adapted to communicate the interior of the LOX container to ambient atmosphere. A vent valve is operatively coupled to the vent line to selectively communicate the interior of the LOX container to the ambient atmosphere. In addition, an auto shutoff assembly is associated with vent line to substantially block the vent line when the LOX in the interior of the LOX container reaches a predetermined level. A reset element is associated with the auto shutoff assembly. The reset element is adapted to reset the auto shutoff assembly by causing at least a portion of the auto shutoff assembly to unblock the vent line.

It is yet another object of the present invention to provide a method of filling a PLOX unit that does not suffer from the disadvantages associated with conventional LOX filling techniques. This object is achieved by providing a method that includes (1) providing a PLOX unit and a LOX supply, (2) coupling the PLOX unit to the LOX supply by manually engaging a first coupling member associated with the PLOX unit with a second coupling member associated with the LOX supply and manually rotating the first coupling member relative to the second coupling member, (3) transferring LOX from the LOX supply to the PLOX unit by manually causing a vent line to communicate an interior of a LOX container in the PLOX unit with ambient atmosphere, and (4) automatically discontinuing the transferring step from the LOX supply to the PLOX unit responsive to the amount of LOX in the PLOX unit reaching a predetermined level.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIG. 4 is a schematic view of the PLOX unit of FIG. 1;

FIGS. 6A and 6B are cross sectional views of a portion of an auto shutoff assembly in the PLOX unit of FIG. 1 showing the position of the valve element relative to the valve seat during the auto shutoff procedure according to the principles of the present invention;

DETAILED DESCRIPTION OF THE EXEMPLARY EMBODIMENTS

Figure 1:
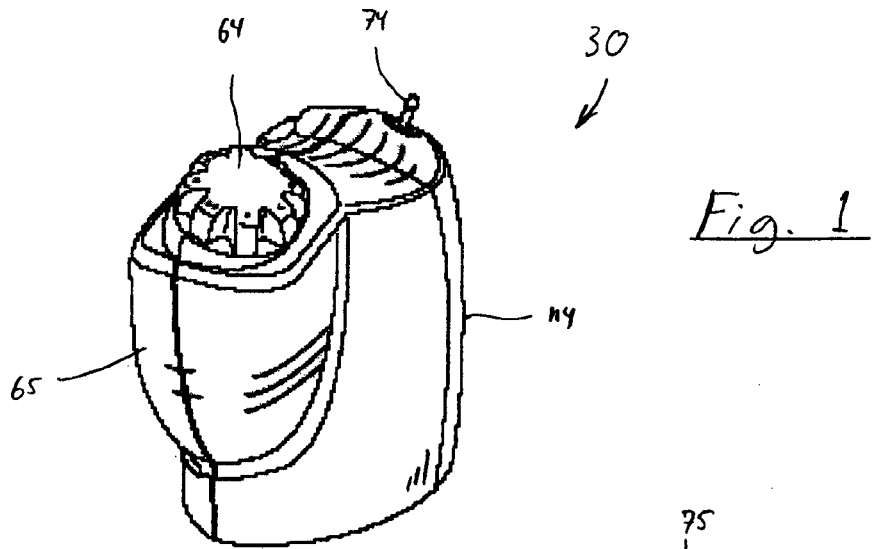
FIG. 1 is a perspective view of a PLOX unit according to the principles of the present invention.
Figure 2:
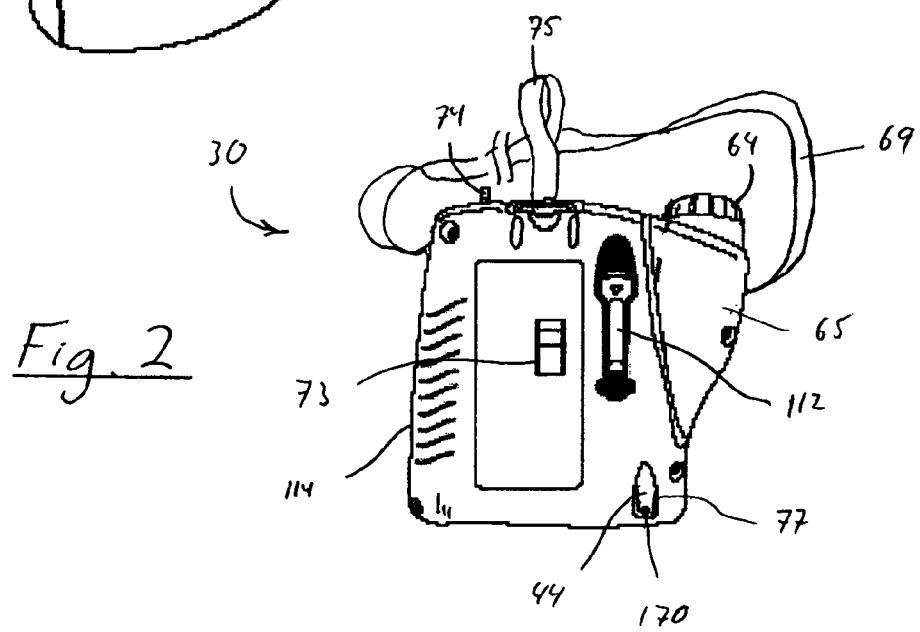
FIG. 2 is a rear view of the PLOX unit of FIG. 1.

An exemplary embodiment of a portable liquid oxygen (PLOX) unit 30 according to the principles of the present invention is described below with reference to FIGS. 1-4. PLOX unit 30 is a small, lightweight liquid gas storage and gas dispensing system. Like conventional portable liquid oxygen delivery units, PLOX unit 30 receives a quantity of LOX from a LOX supply, stores the LOX, and dispenses gas by vaporizing the LOX for consumption by the user. Although unit 30 is referred to as being a LOX storage and dispensing system, it is to be understood that the present invention contemplates that the system of the present invention is capable of storing and dispensing any liquefied gas, combination of gasses, such as helium-oxygen (heliox), or gas mixture.

PLOX unit 30 includes a LOX container 32, also referred to as a LOX storing element or dewer, defining an interior 34 in which liquid oxygen is stored. In the illustrated embodiment, LOX container 32 is generally cylindrical in shape and has a generally domed top wall 36 and domed bottom wall 38. Of course, other shapes for LOX container 32 or portions thereof are contemplated by the present invention. LOX container 32 is made from any material or combination of materials suitable for storing liquid gasses. In FIG. 4, LOX container 32 is shown approximately half full of LOX 33. The remaining portion of interior 34 of LOX container 32 typically contains gas having a high concentration of oxygen due to the evaporation of the LOX in the LOX container.

LOX is provided to LOX container 32 via a LOX receiving system, generally indicated at 39, so that LOX is communicated from a LOX supply to interior 34 of container 32. LOX receiving system 39 includes an inlet line 40 that communicates LOX from a LOX supply 38, see FIGS. 5A-5C, to interior 34 of LOX container 32. As such, inlet line 40 includes a first end portion disposed outside the interior of LOX container 32, and a second end portion disposed in the interior of the LOX container. In the illustrated embodiment, the inlet line enters the LOX container through top wall of the container and terminates near the bottom at the center of the container. It should be noted that inlet line 40, in an exemplary, embodiment loops at least partially around the top of LOX container outside the container to allow for expansion or contraction of the inlet line.

Inlet line 40, which is also know as a fill tube, is used to provide LOX from the LOX supply to LOX container 32, as indicated by arrow A. The flow of LOX along line 40 and into container 32 is indicated by arrows 42. To attach the inlet line to the LOX supply, a first coupling member 44 is provided at the first end portion of the inlet line. First coupling member mates with at associated with the PLOX unit with a second coupling member 46 associated with LOX supply 38. Details an exemplary embodiment of first coupling member 44 and second coupling member 46 are described below with reference to FIGS. 10-13.

LOX container 32 is provided in and is spaced apart from an outer container 48. In an exemplary embodiment, a space 50 is provided between outer container 48 and LOX (inner) container 32. Moreover, space 50 is evacuated to at least a partial vacuum in order to minimize heat transfer to inner LOX container 32. In the illustrated embodiment, outer container 48 is shaped to match the shape of LOX container 32. Thus, in the illustrated exemplary embodiment, outer container 58 is generally cylindrical in shape and has a generally domed top wall and bottom wall. It is to be understood that other shapes for outer container 48 or portions thereof are contemplated by the present invention. Moreover, the shape and size of outer container 48 need not match that of LOX container 32. In addition, the present invention contemplates that outer container 48 is made from any material or combination of materials.

A LOX delivering system, generally indicated at 52, is provided to communicate LOX from the interior of container 32 and, ultimately, for delivery to the airway of user. LOX delivering system 52 includes an outlet line 54, also known as a liquid use tube, having a first end portion disposed outside the interior of LOX container 32 and a second end portion disposed in interior 50 of the LOX container. In the illustrated exemplary embodiment, outlet line 54 is a relatively small diameter hollow tube, for example having an outside diameter of about 1/16 inch as compared to the an outside diameter of 1/4 inch for inlet line 40.

To minimize the number of openings provided in outer container 48 and LOX container 32, the present invention contemplates disposing outlet line 54 within inlet line 40 from the exterior of the outer container. The end of outlet line 54 disposed in LOX container 32 extends from and is spaced apart from the end of inlet of inlet line 40. Outlet line 54 is made from any material or combination of materials suitable to carry a super-cooled liquid, such as LOX. LOX flows into the end of outlet line 54, as indicated by arrow 56 and is carried by the outlet line to a vaporizing coil 58.

LOX is warmed in vaporizing coil 58 so that it changes phase from a liquid to a gas. The outlet of the vaporizing coil is coupled to a pressure relief valve 60.

Should the pressure at the outlet of the vaporizing coil exceed a predetermined threshold, for example due to the evaporation of the LOX, oxygen will vent to the ambient atmosphere through the pressure relieve valve. The venting of gas for the purpose of relieving excess pressure in LOX container 32 is indicated by arrow 59.

In the exemplary illustrated embodiment, LOX delivery system 52 also includes an oxygen conserving device (OCD) 62, which is used, as known in the art, to control the deliver or dosage of oxygen provided to the user. Gas from vaporizing coil 58 is delivered to OCD 62 via conduit 66, as indicated by arrows 70. A flow control knob 64 is used to control the settings for OCD 62. The present invention contemplates that OCD 62 can be any conventional OCD, either pneumatic or electronic. An example of an OCD suitable for use in the present invention is described in U.S. patent application Ser. No. 11/096,993 (publication no. 2006/0219245), the contents of which are incorporated herein by reference.

The use of an OCD enables pulses of oxygen to be delivered to the user during inspiration. That is, the user receive a pulse of oxygen when inhaling but not when exhaling. The frequency of each pulse is determine by the user's breathing rate. By delivering pulses of oxygen only during inhalation, rather than a continuous flow, a single tank of LOX lasts much longer than while still providing the same therapeutic benefit as the continuous flow. Table 1 below lists examples of flow control settings for the flow control knob and the approximate usage time for each setting. Each control setting corresponds to a discrete amount of oxygen that is released to the patient during an inspiratory cycle—the lower the control setting the less oxygen is given during each inhalation. The approximate settings are estimated based on LOX container being full, having 0.9 lbs of LOX, and assuming an average breath rate of 20 breaths per minute (bpm).

TABLE 1

| Flow Control Setting | Approximate Use Time (hours) |
|---|---|
| 1 | 13 |
| 1.5 | 11.5 |
| 2 | 10 |
| 2.5 | 8 |
| 3 | 6 |
| 4 | 5 |
| Continuous Flow (CF) | 2.7 |

It should be noted that other flow control settings are contemplated. In addition, the present invention contemplates eliminating the OCD entirely, so that only a continuous flow of gas is provided to the patient.

Gas from the oxygen conserver is provided to a outlet port 74, also known as a cannula connector or cannula fitting. Gas flows from the outlet port, as indicated by arrow 76. In a typical usage configuration, as known in the art, a flexible tube or cannula is connected to outlet port 74. Gas is delivered to the airway of the user via the flexible tube and interfaces with the airway of the user in any conventional manner, such as to the nares via a pair of nasal prongs or a nasal or nasal/oral mask. It is to be understood that the present invention contemplates using any suitable device or technique for interfacing the flow of gas with an airway of patient, including a conventional nasal cannula or oxygen mask.

In addition to drawing LOX from LOX container 32 for consumption by the user, LOX unit 30 includes a gas delivering system, generally indicated at 80, to communicate gas, such as oxygen, from interior 34 of container 32 and, ultimately, for delivery to the airway of user. As noted above, LOX container 32 will typically include gas having a high concentration of oxygen suitable for consumption by the user. This gas is removed from LOX container 32 by gas delivery system 80 and provided to outlet port 74 via OCD 62.

Gas delivery system 80 includes a gas outlet line 82 having a first end portion disposed outside the interior of the LOX container 32 and a second end portion open and/or disposed in the interior of the LOX container. Gas outlet line 82 is made from any material or combination of materials suitable to a gas. Gas flows into the end of gas outlet line 82, as indicated by arrow 84 and is carried by the outlet line to a warming coil 86, as indicated by arrow 88. Gas from the warming coils is provided to line 66 were it is carried to OCD 62 for consumption by the user. A secondary pressure relief valve 90 is provided in gas delivery system 80 to vent gas to atmosphere, as indicated by arrow 92, if the pressure in interior 34 of LOX container 32 exceeds a threshold.

LOX unit 30 includes a venting system, generally indicated at 100, for communicating the interior of LOX container 32 to ambient atmosphere. Venting system 100 includes a vent line 102 having a first end portion disposed outside the interior of LOX container 32 and a second end disposed in the interior of the LOX container. Gas flows into vent line 102 from the interior of LOX container 32, as indicated by arrow 104, and is carried by the vent line, as indicated by arrows 106. A vent valve 108 is provided at the first end portion of vent line 102 to selectively communicate the interior of the LOX container to the ambient atmosphere. That is, when open, vent valve 108 permits a flow of gas from vent line 102 to ambient atmosphere, as indicated by arrow 110. When closed, vent valve 108 blocks a flow of gas from vent line 102 to ambient atmosphere.

A vent handle 112 is provided for actuating vent valve. Vent handle 112 is exposed on the exterior of a housing 114 or shell that contains the elements of the LOX unit, so that the vent handle can be manually moved by a user between an open position, in which the vent line communicates the interior of the LOX container to the ambient atmosphere, and a closed position that substantially prevents communication of the interior of the LOX container to the ambient atmosphere via the vent line. Details of vent valve 108 are described below with reference to FIG. 14.

PLOX unit 30 includes an automatic shutoff system, generally indicated at 110, that blocks further LOX from entering LOX container 32 once a predetermine level or amount of LOX has been delivered to the LOX container during the filling process. In the embodiment of the present invention illustrated in FIGS. 1-6B, auto shutoff system 110 is associated with vent line 102. The details of the procedure for filling PLOX unit 30 from a supply of LOX and the operation of auto shutoff system 110 are discussed below with reference to FIGS. 4-6B.

Figure 5C:
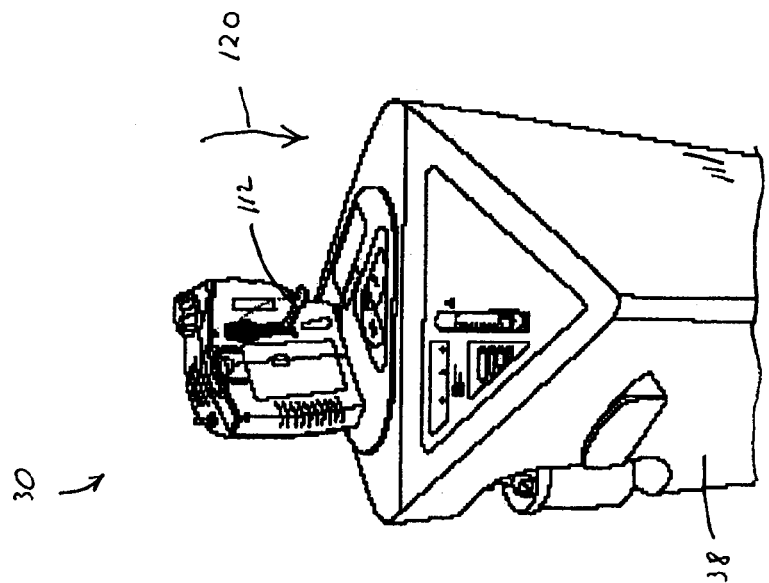
FIGS. 5A-5C are perspective views illustrating steps in the process for filling the PLOX unit of FIG. 1.
Figure 5B:
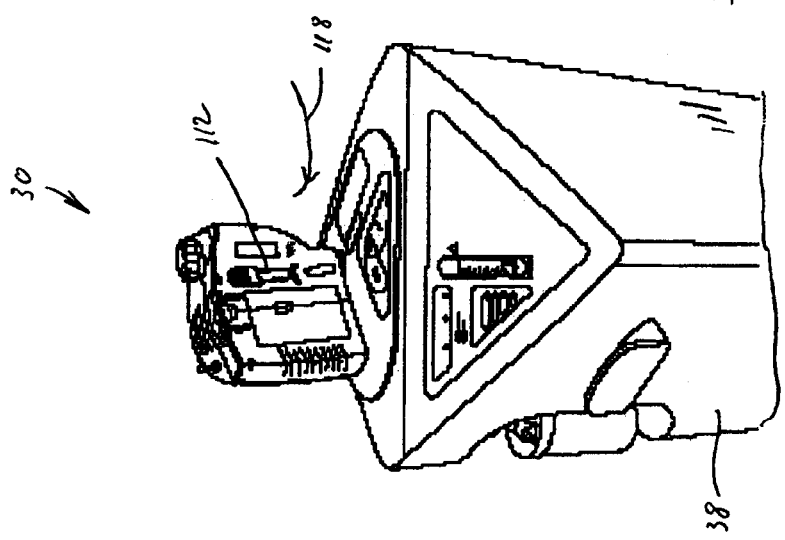
Figure 5A:
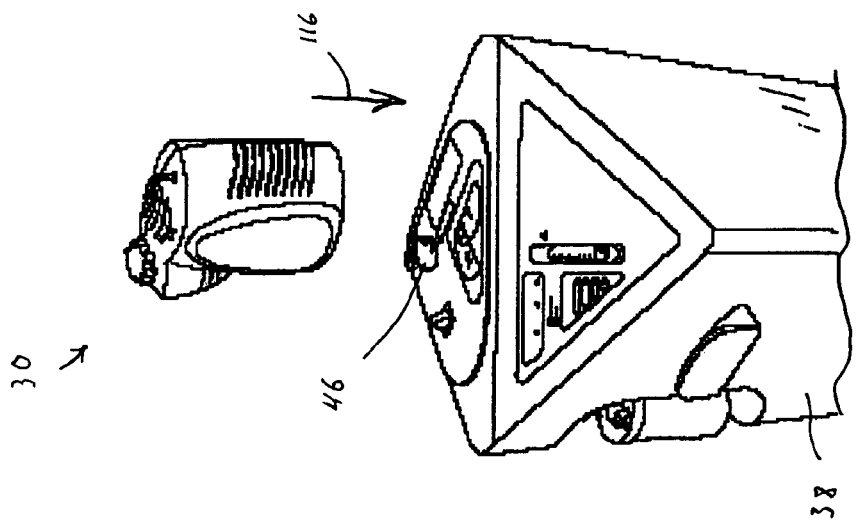

To fill LOX unit 30, the user first places the LOX unit onto a LOX supply 38 so that first coupling member 44 mates with second coupling member 46 on the LOX supply, as indicated by arrow 116 in FIG. 5A. Vent handle 112, i.e., vent valve 108, is in the closed position so that the interior of the LOX container is effectively isolated. In the illustrated embodiment, vent handle 112 is configured such that in the close position it is flush with or recessed into shell 114. This prevents inadvertent movement of the vent handle.

First coupling member 44 and second coupling member 46 are configured such that they engage on another and remain attached or coupled together. To accomplish this function, they may include threads, locking clamps, a slot-and-key configuration, or any other configuration that achieves this goal. In the embodiment illustrated in FIG. 4, a pair of pins are provided on first coupling member 44 engage helical slots (not shown) provided in second coupling member 46. Engaging LOX unit 30 to LOX supply 38 is accomplished by rotating the LOX unit, as indicated by arrow 118 in FIG. 5B, to lock first coupling member 44 onto second coupling member 46. When the LOX unit is fully rotated relative to the LOX supply, it is fully engaged to the LOX supply so that no other or additional force is required by the user to maintain the LOX unit on the LOX supply. In this manner, the present invention provides "hands-free" filling of the LOX unit.

First coupling member 44 includes a one-way valve that is opened when the first coupling member is properly secured to the second coupling member 46. Once properly coupled together, a gas flow path is created from the LOX supply to interior 34 of LOX container 32 via inlet line 40 so that the pressure in interior 34 equalizes with that of the LOX supply. Of course LOX will not flow from the LOX supply into LOX container 32 unless the pressure in the LOX container is less than that of the LOX supply.

To cause a pressure difference between the LOX supply and interior 34 of LOX container 32, the user must move vent handle 112 to the open position, as indicated by arrow 120 in FIG. 5C, thereby opening vent valve 108. This causes interior 34 of LOX container 32 to vent to atmosphere, so that it assumes the atmospheric pressure, i.e., relieving the pressure within the LOX container. Because the atmospheric pressure is now lower than the pressure at which the LOX in the LOX supply is maintained, LOX will flow from the LOX supply into LOX container 32. See arrows A and 42 in FIG. 4. It should be noted that an optional boil-off coil can be provided in vent line 102 to allow any LOX traveling in the vent line to heat, thereby converting it to a gas before being discharged to ambient atmosphere.

Vent valve 108 and/or vent handle 112 are configured such that once the vent handle is moved to the open position, as shown in FIG. 5C, it remains in that position without further interaction from the user. That is, the user need not continue to hold vent handle 112 in the open position. Thus, after manually starting the filling process, LOX will continue to flow from the LOX supply to the LOX unit in a "hands-free" filling operation until the LOX unit is full. For a LOX unit that holds approximately 0.9 lbs of LOX, the filling process typically takes less than 60 seconds.

LOX will continue to flow from the LOX supply into LOX container 32 until it is automatically shutoff by auto shutoff system 110. Details of the auto shutoff system are shown in FIGS. 6A and 6B. As can be appreciated from reviewing these figures, auto shutoff system 110 includes a valve assembly associated with vent line 102 that substantially blocks the vent line when LOX 33 in interior 34 of LOX container 32 reaches a predetermined level. Blocking the vent line removes the path to atmosphere, so that pressure begins to build up on the interior of the LOX container. In other words, the pressure P1 in LOX container 32 will increase until it equalize the pressure of the LOX supply. When these pressures are equal, LOX will cease to flow from the LOX supply into the LOX container.

The valve assembly portion of auto shutoff system 110 includes a moveable valve element 122 and a valve seat 124. In the illustrated exemplary embodiment, moveable valve element 122 is a ball valve having a density that allows it to float on LOX. In an exemplary embodiment of the present invention, moveable valve element 122 is formed form Teflon or a metallic material.

Valve seat 124 is configured as a generally conical shaped or tapered surface against which the ball valve can seal. Moveable valve element 122 and valve seat 124 are also configured, sized, and arranged such that the moveable valve element can rest on the valve seat and substantially block a flow of gas or fluid through to vent line 102. More specifically and as shown in FIGS. 6A and 6B, as LOX 33 fills LOX container 32, the level of the LOX lifts valve element 122 into valve seat 124, substantially sealing vent line 102. Valve element 102, in effect, acts as a float valve to seal against valve seat 104. As noted above, sealing off or blocking vent line 102 causes the pressure P1 in LOX container 32 to equalized with that of the LOX supply. It is to be understood that moveable valve element 122 and a valve seat 124 can have a variety of configurations so long as the sealing function can be accomplished.

A valve element retaining structure or holder 126 is provided for controlling the position valve element 122 relative to valve seat 124. Valve element retaining structure 126 ensures that valve element 122 remains positioned and aligned with the valve seat as the level of LOX in the LOX container changes. It also prevents the valve element from moving too far away from the valve seat. In addition, valve element retaining structure 126 and valve element 122 are configured, sized, and arranged such that the valve element can move freely within an interior 127 of the valve element retaining structure. A plurality of openings 128 are provided in the wall of valve element retaining structure 126 so that the LOX can flow freely through the valve element retaining structure.

Valve element retaining structure 126 is also configured and arranged to prevent valve element 122 from "jumping" of the valve element into the valve seat. As the filling of the LOX into LOX container 32 takes place, gas will flow into the end of inlet line 102. If the ball valve element is retained to close to the opening of the inlet line, the ball will be sucked or jump into the opening, thereby stopping the filling process prematurely. Thus, the cylindrical cage-like configuration for valve element retaining structure 126 is provided to allow a large amount of gas flow around the ball valve element into the opening of the vent line. The structure for valve element retaining structure 126 also dampens turbulence of the LOX around valve element 122, again to prevent the valve element from being prematurely pushed into a engagement with the valve seat.

The present invention contemplates that valve element retaining structure 126 can have any number of a variety of configurations, including different configurations, sizes, shapes, and numbers of opening 128, so long as the functions noted above are achieved. For example, in FIG. 3 of the parent application, the retaining structure is configured as a spiral or helical wire or mesh. In another embodiment, the porosity of the valve element retaining structure, i.e., the size and/or distribution of opening 128, changes over the length of the valve element retaining structure. In an exemplary embodiment of the present invention, valve element retaining structure 126 is formed from Teflon or another non-metallic substance.

Returning again to the auto shutoff function, as the level of LOX 33 in LOX container 32 reaches a maximum capacity, the floating ball valve element 122 is lifted by the LOX toward the opening of the vent line 102. Prior to valve element 122 sealing against valve seat 124, the pressure P1 in the interior of LOX container 32 will be less that that of the LOX supply. At this point in the filling process, pressure P1 in the interior of LOX container 32 is less than the pressure of the LOX supply and LOX flows from the LOX supply into the LOX container. When the valve element seals against the valve seat, a pressure differential is created on either side of the valve element. More specifically, the pressure in an interior 130 of valve line 102 is at atmospheric pressure P2 (due the vent valve 108 being open), while the pressure P1 in the interior of the LOX container is now generally equal that of the LOX supply, which is a higher pressure than P2, and LOX has ceased flowing from the LOX supply into the LOX chamber. In short, plugging vent line 102 causes the pressure in LOX container 132 to again equalize with the pressure in the LOX supply, and the filling process will stop.

Once the flow of LOX the LOX supply into the LOX chamber has ceased, LOX unit 30 can now be removed from LOX supply 38. It should be noted that during the filling process, a flow of gas will be exhaust to atmosphere through vent line 102. This is due to the LOX replacing the gas in the volume of the LOX container. Once valve element 122 plugs vent line 102, the flow of gas to atmosphere through vent line 102 will also stop. The present invention contemplates that the flow of gas through vent line 102 and vent valve 108 will have a distinct sound. Thus, as long as the user hears this sound, they will know that filling is taking place. Once the sound stops, the filling has ended. To enhance this audible filling sound feature, the present invention contemplates providing a sound generating device, such as a whistle, rattle, or vibration, that is created by the flow of gas through vent line 102 and/or out of vent valve 108.

Once the filling process has ended, the user closes vent handle 112, rotates the LOX unit in the direction opposite that shown in FIG. 5B, and lifts the filled LOX unit from the LOX supply. It can be appreciated that at this point, a low pressure P2 exists in interior 130 of vent line 102 on one side of valve element 122, and a higher pressure P2 exists in interior 34. This pressure differential will cause the valve element to remain seated on valve seat 124 even if the level of LOX is lowered so that the valve element is no longer floating on the LOX. Unless valve element 122 is moved off of valve seat 124, it would not be possible to refill the LOX chamber.

The present invention addresses this by providing a reset element or resetting system associated with auto shutoff assembly 110. The reset element is adapted to reset the auto shutoff assembly by moving at least a portion of the auto shutoff assembly to unblock the vent line. In the embodiment illustrated in FIG. 4, the resent element is in the form of a reset orifice 132 provided in vent line 102. As described below, the function of reset orifice 132 is to cause valve element 122 to become unseated from valve seat 124, thereby unblocking vent line 102 so that the LOX unit can be filled again.

Reset orifice 132 defined in vent line 102 between valve seat 124 and the first end portion of the vent line. More specifically, the reset orifice is configured and arranged so as to communicate interior 130 of the vent line with interior 34 of the LOX container 32. The size of reset orifice 132 is substantially smaller than the opening of vent line 102. Accordingly, reset orifice 132 permits only a nominal amount of gas or LOX to flow from LOX container 32 to vent line 102. It can be appreciated that the reset orifice can have configurations other than that shown in FIGS. 4, 6A and 6B. Also, multi reset orifices can be provided.

Reset orifice 132 is defined in vent line 102 as a location that enables the reset orifice to always remains open even after a valve element 122 closes the opening of vent line 102. Thus, once LOX container 32 is full and if vent valve 108 remains open, a small out gas may escape to ambient atmosphere through the reset orifice and the vent line. This may happen, for example, as the LOX in LOX container 32 evaporates into oxygen gas.

The present invention contemplates configuring reset orifice 132 to emit a distinct and audibly different sound than any sound associated with the flow of gas through vent line 102 and/or vent valve 108. In other words, before valve element 122 seals vent line 102, little or no sounds may made by gas (or LOX) passing into vent line 102. However, after valve element 122 seals the opening to vent line 102, gas or LOX can pass from LOX container 32 into vent tube 102 through reset orifice 132. This will cause a distinct sound, such as a whistle or hum, due to the gas or LOX passing through reset orifice 132, thus providing a distinct and positive audible indication that the LOX unit is full, as opposed to the end cessation of sound associated with the termination of the flow of exhaust gas through the vent line discussed above.

Resetting orifice 132 slowly allows the pressure P2 in vent line 102 to equalize with the pressure P1 in LOX container 32. That is, the pressure on either side of valve element 122 equalizes as a result of the reset orifice, so that there is no longer a pressure differential between each side of the valve element. Once the pressure differential on each side of the valve element is reduced, the force of the weight of the valve element will eventually overcome the force holding the valve element against valve seat 124, causing the valve element to drop or become unblocked from the valve seat, thus resetting the LOX unit for the next filling procedure and preventing floating shutoff ball valve element 122 from perpetually blocking the opening of vent line 102. Once released, valve element 122 will continue to float on the LOX as the level of LOX goes down, typically as a result of the user receiving oxygen from the LOX unit.

It can be appreciated that the LOX filling process has three primary mechanisms, which, used in tandem, allows the user to safely and effectively fill LOX unit 30 "hands free". The three mechanisms are (1) a locking fill connector that locks the LOX unit onto the LOX supply so that the user need not hold the portable unit in place on the stationary unit, (2) a latching vent valve handle so that the can manually indicate the LOX filling process and the LOX filling process will continue "hands free", and (3) an auto shutoff system to automatically cease the flow of LOX to LOX unit 30 once it is full so that the user need not maintain a constant vigil over the LOX unit during the filling process. Moreover, filling will terminate even if the user leave the LOX unit unattended during the filling process. For example, if the user forgets about it during filling, the LOX unit will cease filling, as described above, avoiding the waste of oxygen. After filling, the user can then shut the vent valve and detach the LOX unit from the LOX supply.

The automatic, hands-free, filling technique of the present invention takes the user interaction out of the filling process equation by locking the LOX unit to the liquid source, venting, and terminating the fill on its own. The automatic filling technique not only simplifies the filling process for the user, but it ensures that the LOX unit is safely filled to the appropriate liquid level. The user is not required to awkwardly hold the system in place, open the vent circuit, and make a subjective judgment as to whether the system is full while cold gaseous and possibly liquid oxygen could be venting from the system.

Table 2 below summarizes exemplary specifications for LOX unit 30. It is to be understood that these parameter are merely examples, and that other vales for each item of the LOX unit are contemplated by the present invention.

TABLE 2

| | |
|---|---|
| Weight | 3.8 lbs (full) or less |
| | 2.7 lbs (empty) or less |
| Height | 8 inches or less |
| Length | 8 inches or less |
| Width | 4 inches or less |
| Duration | 10 hrs (determined at pulse mode selection 2 at a breathing rate of 20 bpm) or more |
| Modes of Operation | 1, 1.5, 2, 2.5, 4 and 4 (pulse mode) |
| | CF (2 slm continuous flow) |
| Refill Time | <60 seconds |
| Pressurized Normal | 0.5 lb/day (min) |
| Evaporation Rate | 1.0 lb/day (max) |
| OCD Type | Pneumatic or Electronic |
| Cannula Type | Single Lumen or Dual Lumen |

It can be appreciated from the foregoing description, that the PLOX filling system of the present invention eliminates both the need for the user to use one or more hands during the filling process, as well as the need for the user to use his/her judgment as to whether the system is full. The present PLOX filling system takes the user's interaction out of the filling process by locking the PLOX system to the liquid source and terminating the fill on its own.

Figure 7:
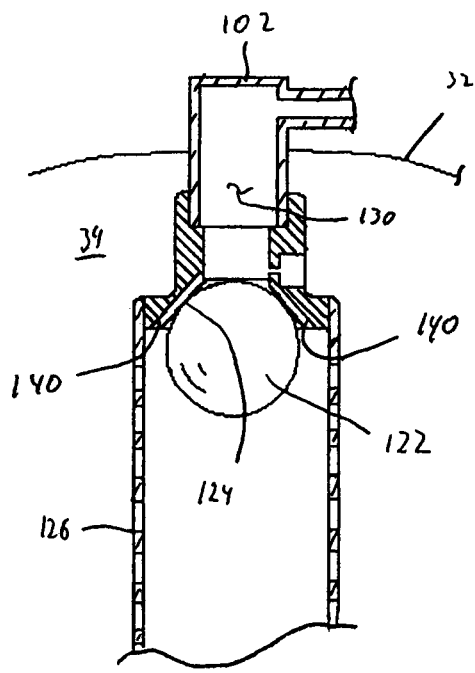
FIGS. 7-9 illustrate alternative embodiments for the auto shutoff portion of the PLOX unit according to the principles of the present invention.

The present invention contemplates other technique for resetting valve element 122 after the termination of the filling process. In a further embodiment, the resetting orifice is, in effect relocated. However, a path is still provided that serves the function of the resetting orifice, i.e. to slowly equalize the pressure on each side of the moveable valve element. For example, as shown in FIG. 7, the resetting orifice is formed as one or more channels 140 provided in valve seat 124. The present invention contemplates eliminating resetting orifice 132 in favor of providing a seal between valve seat 124 and valve element 122 that has a small intentional leak. This is also the result achieved in the embodiment of FIG. 7 in which the valve seat is effectively an incomplete seal due the present of channels 140.

Figure 8A:
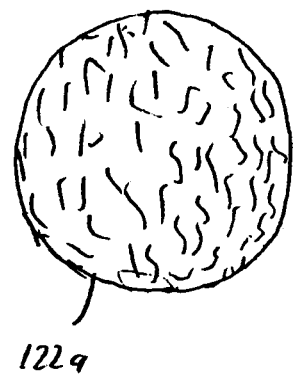
Figure 8B:
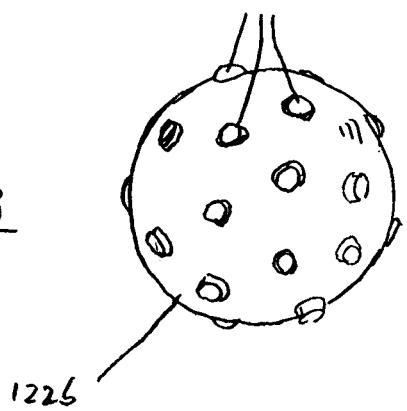

In another embodiment shown in FIGS. 8A and 8B, a small, intentional leak or reset space is provided between the moveable valve element and the valve seat by providing a roughed or non-smooth surface for the valve element. In FIG. 8A, valve element 122a includes a roughed surface so that a multitude of minute gas pathways are created over the surface of the ball valve. This allows gas to leak slowly around the valve element even while it is seated on the valve seat. In the embodiment shown in FIG. 8B, valve element 122b includes a plurality of nodules 142. These nodules, which can have shape, size, pattern, or configuration, prevent a complete seal from being forming when the valve element engage the valve seat. Again, this reset space between the valve element and the valve seat accomplishes the function of resetting orifice 132 of slowly equilibrating the pressure on each side of the moveable valve element.

Figure 9:
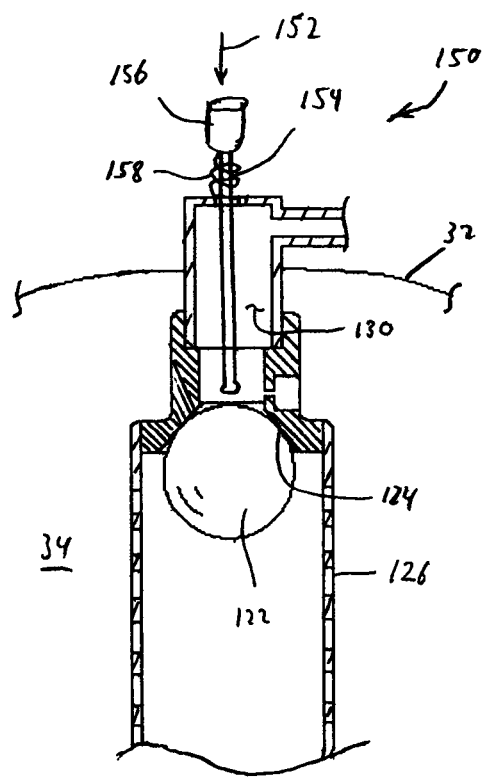
Figure 10:
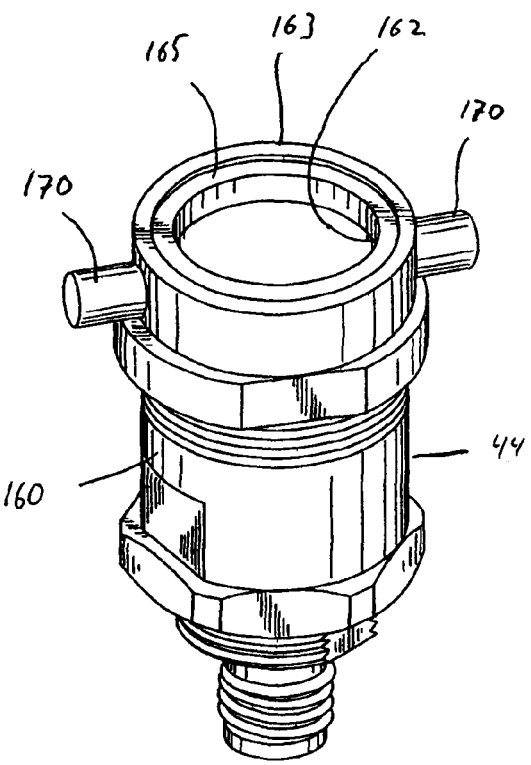
FIG. 10 is a perspective view of a first (male) coupling member suitable for use in the PLOX unit of the present invention.
Figure 11:
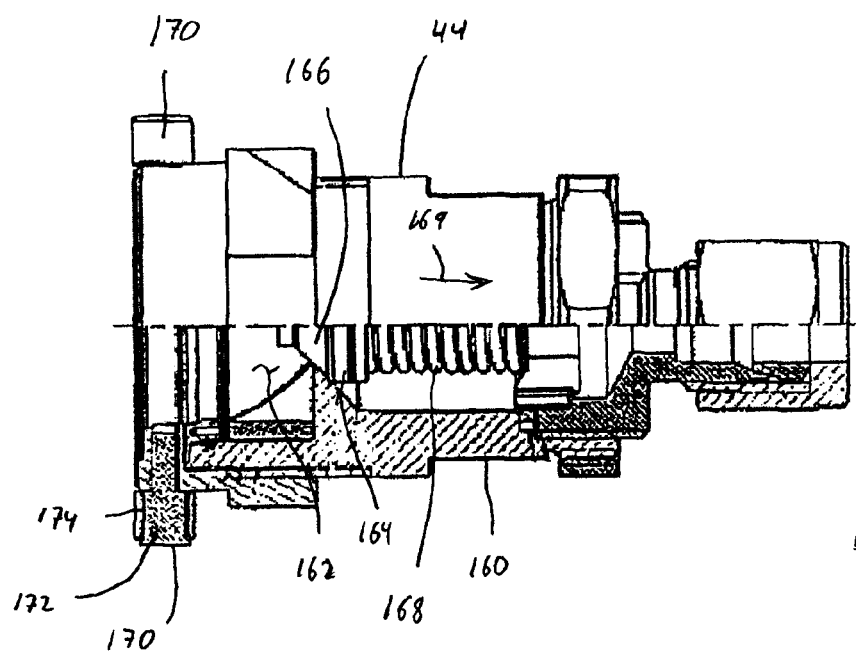
FIG. 11 is a partial cross-sectional view of the first coupling member of FIG. 10.
Figure 12:
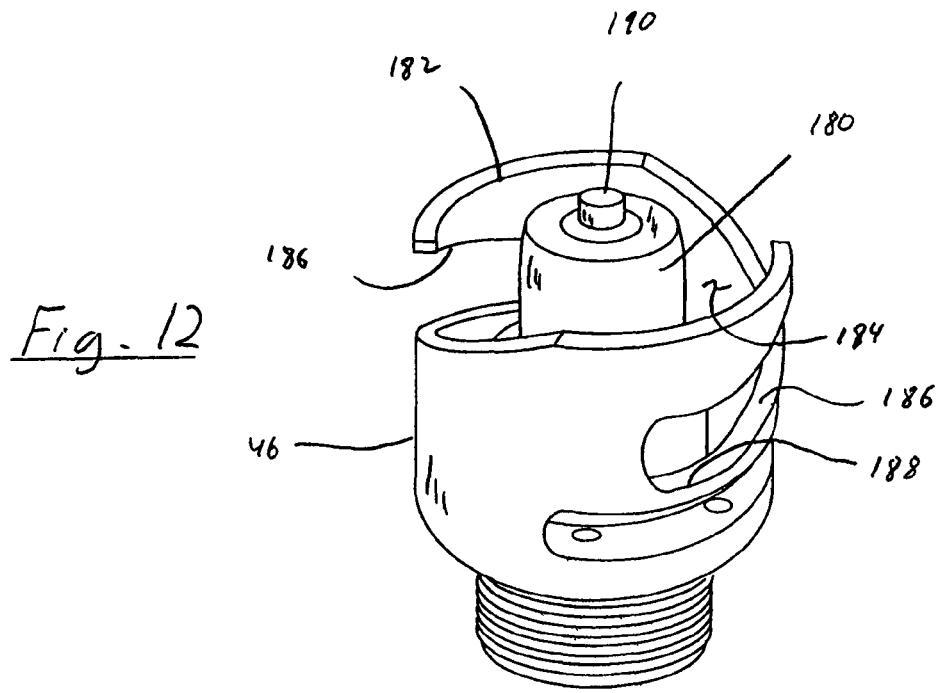
FIG. 12 is a perspective view of a second (female) coupling member suitable for use in the PLOX unit of the present invention.

FIG. 9 illustrates yet another technique for unblocking the valve element form the valve seat. In the embodiment, however, the valve elements is manually removed from the valve seat by applying a removing force of the valve element of sufficient magnitude to overcome the force created be the pressure differential existing on either side of the valve element. A mechanical assembly 150 is provided to apply a force, as indicated by arrow 152, on valve element 122 to unseat the valve element from valve seat 124.

In the illustrated exemplary embodiment, mechanical assembly 150 includes an actuating rod 154 that passes through vent line 102 and having distal end that contacts valve element 122. A proximal end of the actuating rod is disposed outside of LOX container and is manually actuated in any conventional manner. For example, a push button 156 may be provided at the distal end of the rod and a return spring 158 can be use to return the actuating rod to its non-actuated position. Of course, a myriad, of different types of mechanical assemblies can be used to manually and forcibly unseat valve element 122 from the valve seat. Preferably, a thermal isolating mechanism is used to prevent heat from entering the LOX chamber via mechanical assembly 150.

Although the present invention has been described above has having a single valve element that float on the LOX, the present invention contemplates that multiple valve elements can be provided. Any one of the valve elements can block the valve seat when the level of LOX is high enough to move the valve element in proximity to the valve seat. In this embodiment, valve element retaining structure 126 can be sized and configured so as to house the multiple valve elements, or the valve element retaining structure 126 can be omitted entirely. In this latter case, a sufficient number of valve elements, floating on the LOX, should be provided so that one of the valve elements is sure to move to a position to block the vent line.

As noted above, one feature of the PLOX unit is its relatively low height.

In an exemplary embodiment, the unit has a height of 8 inches or less. This short height provides several advantages. For example, having a low height lowers the center or gravity for the PLOX unit. This makes the unit more stable when sitting in its normal, upright position. The lower height also aids in making the device more comfortable for the user in certain situations, such as bending and sitting. When bending or sitting, a taller unit can be cumbersome and bulky.

To help reduce the overall height of the unit, OCD 62 and flow control knob 64 used to control the settings for the OCD are set off-center. More specifically, a shoulder is provided that taper inward in the direction toward the bottom of the user. This taper ensures that that the footprint is minimized along with the height.

Yet another feature of the present invention that serves both to minimize the height of the unit while also reducing the weight, is to provide the unit with a non-rigid handle. Some conventional portable LOX delivery apparatus have a rigid handle located on the top of the unit and centered on the unit. While this provides an easily accessible handle, it also adds significantly to the total height of the unit and also to the weight. In an exemplary embodiment of the present invention, a fabric handle 69 or strap is provided, where each end of the handle connects to opposite side of rigid housing 114. The handle can be permanently or removably attached to the housing, using any conventional technique. The length of handle 69 can also be adjustable in any conventional manner. The non-rigid handle can be padded or reinforced to promote strength and/or comfort.

Figure 3:
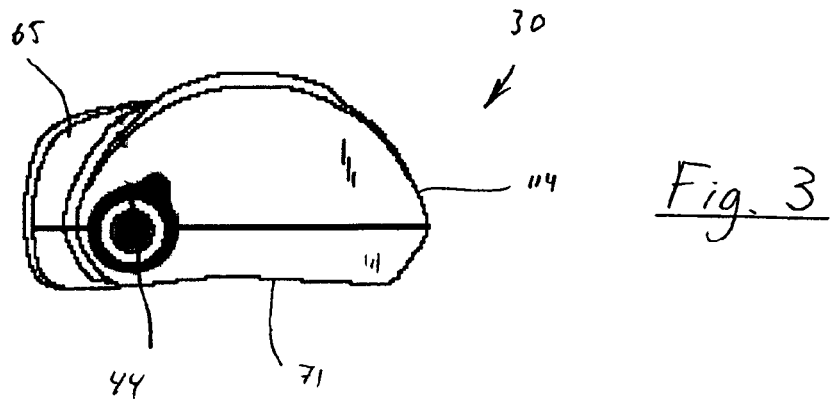
FIG. 3 is a bottom view of the PLOX unit of FIG. 1.

As perhaps best shown in FIG. 3, housing 114 is generally "kidney" shaped to promote comfort when the unit is worn or carried by a user. When worn or carried by a user, side 71 of housing 114 faces the user. This side is provided with a concave shape to hug the body of the user better than a flat or convex surface.

PLOX unit 30 also includes a scale 73 that is visible from the back of the unit. A handle 75 is attached to the scale so that when the user lifts the unit by handle 75, the scale will indicate the weight of the unit. This helps the user determine how much LOX is remaining in the unit. Of course, the scale can have other configurations and can be provided at other locations on the unit. For example, the scale can be provided as a pressure sensor that weighs the unit when it is placed on a flat surface. A digital or analog readout can be provided to tell the user the weight of the unit and/or how much LOX remains. The present invention also contemplates calculating the amount of oxygen use remaining based on the monitored weight and the selected flow rate. Of course, processing elements and output devices would need to be provided to accomplish this function.

In addition, a window 77 is provided at the lower corner near the bottom of housing 114. Window 77 is defined through the housing to provide visual access to first coupling member 44. In the illustrated embodiment, window 77 is tear-drop shaped.

However, the present invention contemplates that the window can have other shapes, sizes, and configurations and may have a clear pane covering the window. Window 77 allows the user to see first coupling member 44 when he or she is attempting to connect the PLOX unit to second coupling member 46 associated with LOX supply 38. Being able to seek the first coupling member assists in the ability of the user to aligning the first coupling member with the second coupling member during the start of the filling process.

Referring now to FIGS. 10-13, the details of first coupling member 44 and second coupling member 46 will be discussed. First coupling member 44, which is associated with PLOX system 30, includes a central housing 160 having a stem receiving cavity 162 defined therein. A one way valve 164 is located in housing 160. Valve 164 includes a moveable valve member 166 biased in the closed position by a biasing force. When open, LOX is free to flow through housing 160. In the illustrated embodiment, this biasing force is provided by a spring 168.

A pair of pins 170 are provided on housing 160. In an exemplary embodiment, each pin 170 includes a stem 172 and an outer casing 172 rotateably mounting on the stem. This allows the outer surface, i.e., the casing, to rotate as the pin engages another surface, thereby reducing friction between the pin and the other surface.

Second coupling member 46 includes a housing having a stem 180 and an outer basket 182 such that a space 184 is defined between the stem and the outer basket. A pair of helical or spiral slots 186 are defined in the outer basket to receive pins 170 from first coupling member 44. The slots includes a portion 188 at the end that is not helical, so that once pin 170 moves to portion 188, the pin remains within the slot. Second coupling member 46 also includes a valve 190.

Engaging first coupling member 44 with second coupling member 46, required inserting stem 180 into stem receiving cavity 162, which also results in placing a wall 163 of housing 160 into space 184. Pins 170 must be aligned with the open ends of helical slots 186. The first coupling member and second coupling member are then pushed toward one another while twisting or rotating one relative to the other so that pins 170 move along slots 186. Valve 190 engages valve 164 causing both to move to an open position. Opening of valve 164 is indicated by arrow 169 in FIG. 11. When fully inserted, an outer edge 165 of wall 163 abuts a shoulder 185 in second coupling member 46. The bias forces that tend to urge valves 164 and 190 in the close position push against each other, which tends to force the first and second coupling members apart. However, they are held together so long as pins 170 are located in flat portions 188 of slots 186. Thus, the user us able to cease forcing the first and second coupling members together with the coupling member remaining engaged to facilitate hands-free filling of PLOX unit 30.

Figure 13:
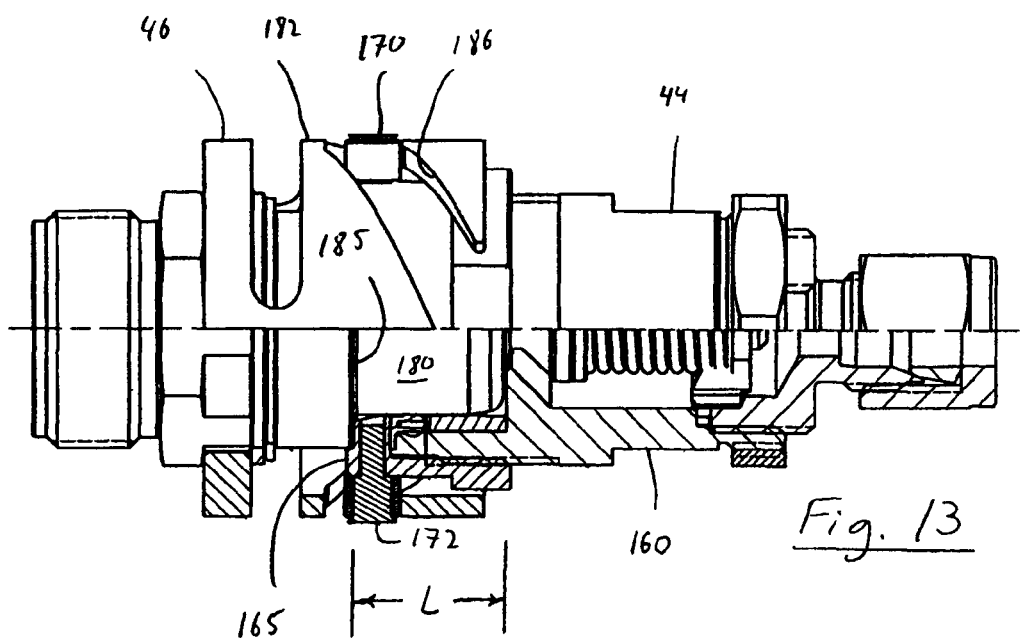
FIG. 13 is a side view, partially in section, showing the first coupling member engaged with the second coupling member.

The length of cavity 162 in first coupling member 44 and the length of stem 180 in second coupling member 46, which is indicated as length "L" in FIG. 13, are selected so that the outer edge 165 of wall 163 abuts a shoulder 185 when the coupling members are engaged. In an exemplary embodiment of the present invention, the overall length of first coupling member 44 and second coupling member 46 is minimized by reducing the length of cavity 162 and stem 180 below that of conventional LOX coupling members. For example, the present invention contemplates that length L is ⅝ inch or less.

Figure 14:
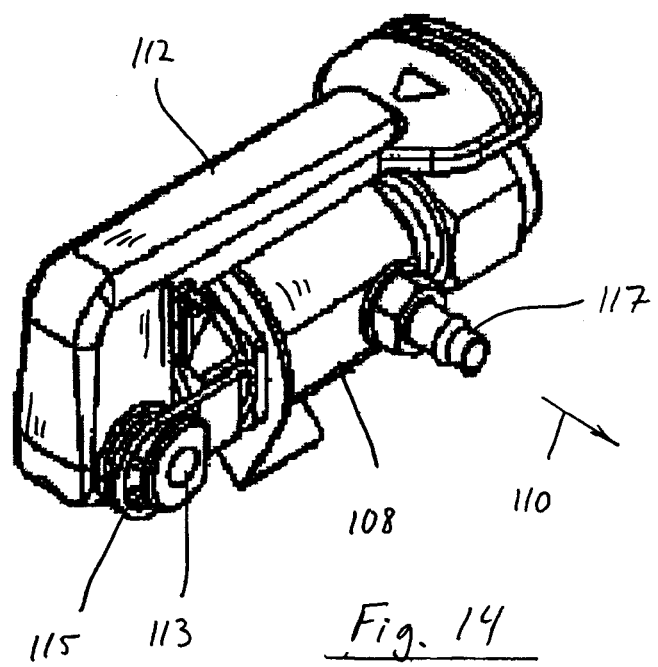
FIG. 14 is a perspective view of a vent valve and vent handle in the venting system used in the PLOX unit according to the principles of the present invention.

FIG. 14 is a perspective view of vent valve 108 and vent handle 112 in the venting system used in the PLOX unit according to the principles of the present invention. Vent valve 1080 is a latching type of valve that, once open, remains open, and once closed, remains close. This facilitates hands-free filling of PLOX unit 30. The present invention contemplates that this latching valve function can be accomplished in a variety of fashions. For example, any mechanical device or structure can be used to maintain vent handle 112 in the open or closed position.

In the illustrated exemplary embodiment, the latching valve function is achieved via cam design of vent handle 112. A cam shaft 113 is provided in an offset location on vent handle 112 so that moving the vent handle about the cam shapes pulls on a vent stem located within the vent valve unseating a portion of the vent stem from a valve seat thereby opening the vent valve. A spring 115 is provided to bias the vent handle and vent stem in the closed position. A barb 117 is also provided as the outlet port for the vent valve. The present invention contemplates connecting a tubing to barb 117 so that the vent gasses can be directed to any desired location in the PLOX unit.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A portable liquid oxygen (PLOX) unit comprising:
   a liquid oxygen (LOX) container having an interior;
   an inlet line having a first inlet end portion disposed outside the interior of the LOX container and a second inlet end portion disposed in the interior of the LOX container, wherein the inlet line is adapted to communicate LOX from a LOX supply to the interior of the LOX container;
   an outlet line having a first outlet end portion disposed outside the interior of the LOX container and a second outlet end portion disposed in the interior of the LOX container, wherein the outlet line is adapted to communicate LOX from the interior of the LOX container;
a vent line having a first vent end portion disposed outside the interior of the LOX container and a second vent end portion disposed in the interior of the LOX container, the vent line further having an interior, wherein the vent line is adapted to communicate the interior of the LOX container to ambient atmosphere;
a vent valve operatively coupled to the vent line to selectively communicate the interior of the LOX container to the ambient atmosphere; and
an auto shutoff assembly associated with the vent line, wherein the auto shutoff assembly includes:
a valve seat defined in the vent line between the first vent end portion and the second vent end portion,
a movable valve element that is buoyant in LOX and is configured such that buoyancy of the valve element in LOX and a rising level of LOX in the interior of the LOX container during filling cause the valve element to engage the valve seat and substantially block the vent line responsive to LOX in the interior of the LOX container reaching a predetermined level of LOX in the interior of the container,
wherein the valve element and/or the valve seat are configured such that, during engagement of the valve element and the valve seat, the interior of the vent line communicates with the interior of the LOX container, wherein such communication between the interior of the vent line and the interior of the LOX container causes a pressure differential between different sides of the movable valve element to be gradually reduced to unblock the vent line, and
wherein the interior of the vent line communicates with the interior of the LOX container through one or more pathways provided by one or more nodules formed on a surface of the valve element and/or on a surface of the valve seat.

2. A portable liquid oxygen (PLOX) unit comprising;
a liquid oxygen (LOX) container having an interior;
an inlet line having a first inlet end portion disposed outside the interior of the LOX container and a second inlet end portion disposed in the interior of the LOX container, wherein the inlet line is adapted to communicate LOX from a LOX supply to the interior of the LOX container;
an outlet line having a first outlet end portion disposed outside the interior of the LOX container and a second outlet end portion disposed in the interior of the LOX container, wherein the outlet line is adapted to communicate LOX from the interior of the LOX container;
a vent line having in a first vent end portion disposed outside the interior of the LOX container and a second vent end portion disposed in the interior of the LOX container, the vent line further having an interior, wherein the vent line is adapted to communicate the interior of the LOX container to ambient atmosphere;
a vent valve operatively coupled to the vent line to selectively communicate the interior of the LOX container to the ambient atmosphere; and
an auto shutoff assembly associated with the vent line, wherein the auto shutoff assembly includes:
a valve seat defined in the vent line between the first vent end portion and the second vent end portion,
a movable valve element that is buoyant in LOX and is configured such that buoyancy of the valve element in LOX and a rising level of LOX in the interior of the LOX container during filling cause the valve element to engage the valve seat and substantially block the vent line responsive to LOX in the interior of the LOX container reaching a predetermined level of LOX in the interior of the container,
wherein the valve element and/or the valve seat are configured such that, during engagement of the valve element and the valve seat, the interior of the vent line communicates with the interior of the LOX container, wherein such communication between the interior of the vent line and the interior of the LOX container causes a pressure differential between different sides of the movable valve element to be gradually reduced to unblock the vent line, and
wherein the interior of the vent line communicates with the interior of the LOX container through one or more pathways provided by a roughed surface on the valve element and/or the valve seat.

3. The unit of claim 2, further comprising:
a shell containing the LOX container such that a vacuum space is provided between the shell and the LOX container, and wherein a vacuum is drawn in the vacuum space; and
a housing containing the shell and the LOX container.

4. The unit of claim 2, wherein interior of the vent line further communicates with the interior of the LOX container through a reset orifice.

5. The unit of claim 2, wherein the interior of the vent line further communicates with the interior of the LOX container through one or more channels formed in the valve seat.

6. The unit of claim 2, wherein the interior of the vent line further communicates with the interior of the LOX container through one or more pathways in a seal between the valve element and the valve seat.

7. The unit of claim 2, wherein at least a portion of the outlet line is disposed within the inlet line.

8. The unit of claim 2, wherein the LOX container includes a top portion, a bottom portion, and a sidewall extending between the top and the bottom, and wherein the inlet line, the outlet line, and the vent line enter the LOX container through the top portion.

9. The unit of claim 2, further comprising a fill connector disposed at the first inlet end portion of the inlet line.

10. The unit of claim 9, wherein the fill connector includes a fill connector locking mechanism adapted to attach the fill connector to a supply connector of a LOX supply and to maintain the fill connector in engagement with the supply connector.

11. The unit of claim 2, further comprising a vent handle associated with the vent valve, wherein the vent handle is manually operable between an open position in which the vent line communicates the interior of the LOX container to the ambient atmosphere and a closed position that substantially prevents communication of the interior of the LOX container to the ambient atmosphere.

12. The unit of claim 9, further comprising a vent valve locking mechanism associated with the vent valve, the vent handle, or both, wherein the vent valve locking mechanism is adapted to maintain the vent handle in the open position responsive to being moved to the open position.

13. A portable liquid oxygen (PLOX) unit comprising:
storing means for storing liquid oxygen (LOX);
LOX receiving means for communicating LOX from a LOX supply to an interior of the storing means;
LOX delivering means for communicating LOX from e interior of the storing means;

venting means for communicating the interior of the storing means to ambient atmosphere the venting means having an interior;

blocking means disposed within the storing means for substantially blocking the venting means responsive to LOX in the interior of the storing means reaching a predetermined level and forcing the blocking means to block the venting means through buoyancy of the blocking means to prevent LOX from entering the storing means; and resetting means for providing gas communication between the interior of the venting means and the interior of the storing means so as to gradually reduce a pressure differential between different sides of the blocking means to move the blocking means and unblock the venting means, wherein the blocking means comprises a movable valve element, wherein the venting means includes a valve seat, wherein the valve element and the valve seat are configured such that the valve element engages the valve seat to substantially block the venting means responsive to LOX in the storing means reaching the predetermined level, and wherein the resetting means comprises one or more pathways provided by one or more nodules formed on a surface of the valve element.

14. A portable liquid oxygen (PLOX) unit comprising:
storing means for storing liquid oxygen (LOX);
LOX receiving means for communicating LOX from a LOX supply to an interior of the storing means;
LOX delivering means for communicating LOX from the interior of the storing means;
venting means for communicating the interior of the storing means to ambient atmosphere, the venting means having an interior;
blocking means disposed within the storing means for substantially blocking the venting means responsive to LOX in the interior of the storing means reaching a predetermined level and forcing the blocking means to block the venting means through buoyancy of the blocking means to prevent LOX from entering the storing means; and
resetting means for providing gas communication between the interior of the venting means and the interior of the storing means so as to gradually reduce a pressure differential between different sides of the blocking means to move the blocking means and unblock the venting means,
wherein the blocking means comprises a movable valve element, wherein the venting means includes a valve seat, wherein the valve element and the valve seat are configured such that the valve element engages the valve seat to substantially block the venting means responsive to LOX in the storing means reaching the predetermined level, and
wherein the resetting means comprises one or more pathways by a roughed surface on the valve element.

15. The unit of claim 14, further comprising:
a shell containing the storing means such that a vacuum space is provided between the shell and the storing means; and
housing means for containing the shell and the storing means.

16. The unit of claim 14, wherein the resetting means comprises a reset orifice.

17. The unit of claim 14, wherein the resetting means comprises one or more channels formed in the valve seat.

18. The unit of claim 14, wherein the resetting means comprises one or more pathways between the valve element and the valve seat.

19. The unit of claim 14, wherein the LOX receiving means includes means for coupling the unit to a LOX supply and for maintaining the unit in a coupled relation to the LOX supply.

20. The unit of claim 14, wherein the venting means includes manual actuating means for communicating the interior of the storing means with ambient atmosphere in an open position and substantially preventing communication of the interior of the storing means to ambient atmosphere in a closed position.

21. The unit of claim 20, further comprising means for maintaining the manual actuating means in the open position without interaction from a user.

22. A method of filling a portable liquid oxygen (PLOX) unit, comprising:
providing a PLOX unit and a liquid oxygen (LOX) supply;
coupling the PLOX unit to the LOX supply by manually engaging a first coupling member associated with the PLOX unit with a second coupling member associated with the LOX supply,
transferring LOX from the LOX supply to the PLOX unit by manually opening a vent line to communicate an interior of a LOX container in the PLOX unit with ambient atmosphere, the vent line having an interior;
providing a substantial blockage of the vent line responsive to LOX in the interior of the LOX container reaching a predetermined level and forcing a moveable valve element to block the vent line through buoyancy;
automatically discontinuing the transferring step from the LOX supply to the PLOX unit responsive to pressure of the LOX in the PLOX unit reaching a pressure of the LOX supply; and
removing the blockage by gradually reducing a pressure differential between different sides of the moveable valve element by providing gas communication between the interior of the vent line and the interior of the LOX container,
wherein the interior of the vent line communicates with the interior of the LOX container through one or more pathways provided by one or more nodules formed on a surface of the movable valve element.

23. A method of filling a portable liquid oxygen (PLOX) unit, comprising:
providing a PLOX unit and a liquid oxygen (LOX) supply;
coupling the PLOX unit to the LOX supply by manually engaging a first coupling member associated with the PLOX unit with a second coupling member associated with the LOX supply;
transferring LOX from the LOX supply to the PLOX unit by manually opening a vent line to communicate an interior of a LOX container in the PLOX unit with ambient atmosphere, the vent line having an interior;
providing a substantial blockage of the vent line responsive to LOX in the interior of the LOX container reaching a predetermined level and forcing a moveable valve element to block the vent line through buoyancy;
automatically discontinuing the transferring step from the LOX supply to the PLOX unit responsive to pressure of the LOX in the PLOX unit reaching a pressure of the LOX supply; and
removing the blockage by gradually reducing a pressure differential between different sides of the moveable valve element by providing gas communication between the interior of the vent line and the interior of the LOX container, wherein the interior of the vent line communicates with the interior of the LOX container through one or more pathways provided by a roughed surface on the moveable valve element.

24. The method of claim 23, wherein as a result of the coupling step, the PLOX unit remains coupled to the LOX supply without manual interaction with the PLOX unit.

25. The method of claim 23, wherein coupling the PLOX unit to the LOX supply includes manually rotating the first coupling member relative to the second coupling member.

26. The method of claim 23, further comprising;
    manually closing the vent line to substantially prevent communication of the interior of a LOX container with ambient atmosphere.

27. The method of claim 23, further comprising uncoupling the first coupling member from the second coupling member responsive to the transfer of LOX to the PLOX unit discontinuing.

* * * * *